(12) United States Patent
Fischer

(10) Patent No.: US 8,038,676 B2
(45) Date of Patent: Oct. 18, 2011

(54) ELECTROSURGICAL INSTRUMENT

(75) Inventor: Klaus Fischer, Nagold (DE)

(73) Assignee: ERBE Elektromedizin GmbH, Tübingen (DE)

( * ) Notice: Subject to any disclaimer, the term of this patent is extended or adjusted under 35 U.S.C. 154(b) by 1182 days.

(21) Appl. No.: 11/568,413

(22) PCT Filed: Apr. 27, 2005

(86) PCT No.: PCT/EP2005/004525
§ 371 (c)(1),
(2), (4) Date: May 23, 2007

(87) PCT Pub. No.: WO2005/110264
PCT Pub. Date: Nov. 24, 2005

(65) Prior Publication Data
US 2007/0293858 A1 Dec. 20, 2007

(30) Foreign Application Priority Data

May 14, 2004 (DE) .......................... 10 2004 024 052
May 28, 2004 (DE) .......................... 10 2004 026 179

(51) Int. Cl.
*A61B 18/18* (2006.01)
(52) U.S. Cl. ................. 606/51; 606/41; 606/42; 606/45; 606/48
(58) Field of Classification Search ............... 606/50–52
See application file for complete search history.

(56) References Cited

U.S. PATENT DOCUMENTS

| | | | |
|---|---|---|---|
| 2,031,682 A * | 2/1936 | Wappler et al. ............... 606/46 |
| 4,498,475 A | 2/1985 | Schneiderman |
| 4,655,216 A * | 4/1987 | Tischer ........................ 606/51 |
| 6,059,782 A | 5/2000 | Novak et al. |
| 6,267,761 B1 | 7/2001 | Ryan |
| 6,270,497 B1 | 8/2001 | Sekino et al. |
| 2001/0037109 A1 | 11/2001 | Yamauchi et al. |
| 2002/0068951 A1 | 6/2002 | Burbank et al. |
| 2002/0128650 A1 * | 9/2002 | McClurken ................... 606/48 |
| 2003/0014052 A1 * | 1/2003 | Buysse et al. ................ 606/50 |
| 2003/0144660 A1 * | 7/2003 | Mollenauer .................. 606/45 |
| 2004/0049185 A1 | 3/2004 | Latterell et al. |
| 2006/0224158 A1 * | 10/2006 | Odom et al. .................. 606/51 |

FOREIGN PATENT DOCUMENTS

DE 2019891 B2 11/1971
(Continued)

*Primary Examiner* — Linda Dvorak
*Assistant Examiner* — Jaymi Della
(74) *Attorney, Agent, or Firm* — Dickstein Shapiro LLP

(57) ABSTRACT

The invention relates to an electrosurgical instrument that comprises two branches joined to one another in an articulated manner, which can be actuated to open or close in a manner corresponding to a clamping, spreading or cutting tool. The instrument further comprises electrode parts at distal ends of the branches, which are used for grasping tissue and passing a coagulation current through the tissue for the purpose of coagulating it and which are electrically insulated from one another, as well as current-supply devices to supply the coagulation current to the electrode parts. In addition, on at least at one electrode part, a cutting section designed as a cutting electrode is provided whereby the electrode part comprises the cutting section and a coagulation section. In addition a control unit is provided to control the HF current in such a way that when a threshold value characterizing a particular property of the grasped tissue has been reached, a cutting current different from the coagulation current is supplied to at least the cutting section.

18 Claims, 4 Drawing Sheets

FOREIGN PATENT DOCUMENTS

| | | |
|---|---|---|
| DE | 4126609 | 2/1993 |
| DE | 4135185 | 4/1993 |
| DE | 19730724 | 1/1998 |
| DE | 19915060 | 11/2000 |
| EP | 0253012 | 1/1988 |
| JP | 2000-135222 A | 5/2000 |
| WO | PCT/EP03/05439 | 5/2003 |
| WO | PCT/US03/28539 | 9/2003 |

* cited by examiner

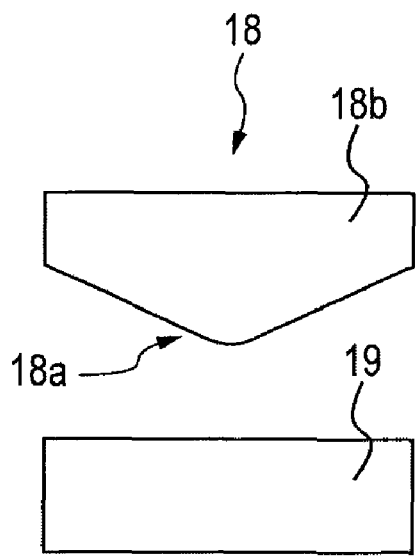
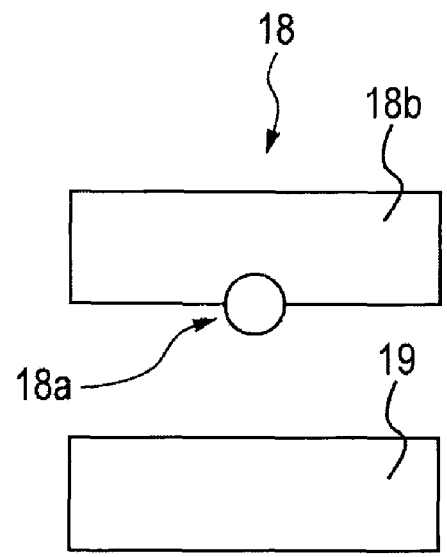
FIG. 1   FIG. 2
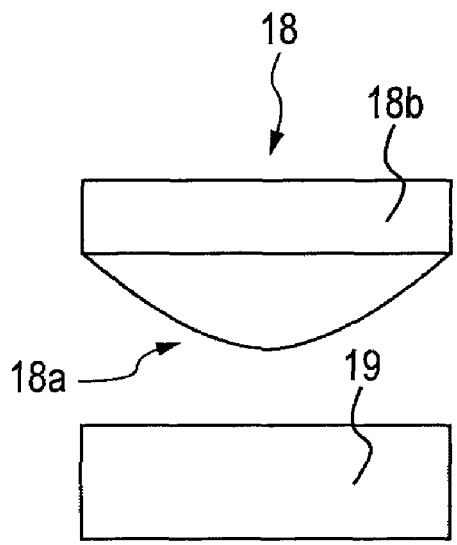
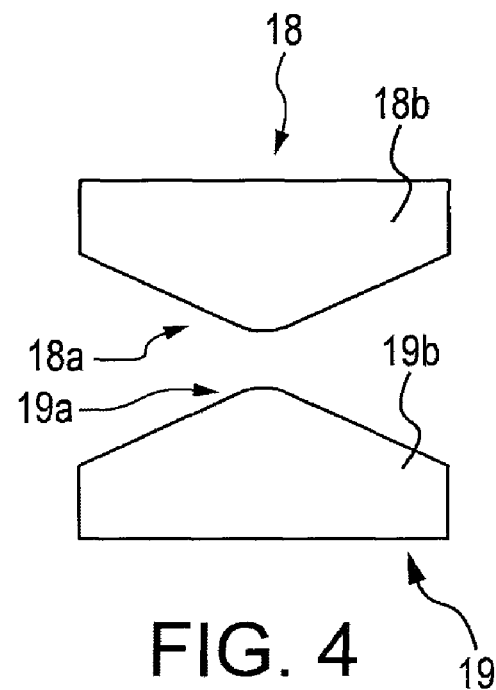
FIG. 3   FIG. 4

ELECTROSURGICAL INSTRUMENT

CROSS-REFERENCE TO RELATED APPLICATIONS

This application is a national stage application under 35 U.S.C. §371 of PCT/EP05/04525, filed Apr. 27, 2005.

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention relates to an electrosurgical Instrument.

BACKGROUND OF THE INVENTION

Electrosurgical instruments have been used for many years in high-frequency surgery, in order to coagulate and/or cut biological tissue. In this process a high-frequency current is conducted through the tissue to be treated, so that the latter becomes altered owing to protein coagulation and dehydration. The tissue thus contracts in such a way that the vessels are closed and bleeding is stanched. A subsequent increase in current density causes an explosion-like evaporation of the tissue fluid and tearing apart of the cell membranes, so that the tissue is completely transected. Procedures of this kind present the advantage, as opposed to a purely mechanical cutting process, that hemostasis is produced at the cut edges.

The employment of bipolar instruments is becoming increasingly significant, because the current intensities are less than in the case of monopolar instruments. It is especially advantageous that the current route between the electrode parts of bipolar instruments can be calculated and does not pass for large distances through the patient's body.

Bipolar instruments comprise substantially two clamp parts having an articulated connection to one another, with gripping devices provided at their proximal ends for manipulation of the clamp parts. At distal ends of the clamp parts there are electrode parts for grasping tissue and for conducting a coagulation current through the tissue. The HF current generated by a HF generator is conducted to the electrode parts of the bipolar instrument by way of current-supply devices.

When the bipolar instruments described above are being used, after a coagulation procedure cutting instruments must be employed for the final transection of the coagulated tissue. The cut is carried out with either a surgical scissors or a HF cutting instrument. However, this use of different instruments requires interruption of the surgical operation, which is thus unnecessarily prolonged.

To counteract this disadvantage, multifunctional instruments have meanwhile come into use, designed at least for both coagulation and cutting. Such an instrument is known, for example, from the document DE 199 15 060 A1, with which diverse working devices such as forceps, hooks or even ultrasonic devices and electrodes for cutting or coagulation can be put into operation by actuators. A control unit enables the planned working steps to be carried out consecutively.

The embodiment of a multifunctional instrument described there, however, has the disadvantage that coagulating and cutting are still two different treatments, to be performed successively in time, even though the steps can be carried out by single instrument. A first procedure must therefore be intentionally ended, after which a second procedure is, again intentionally, begun. Between these procedures at least one manipulation must be done, namely to activate the multifunctional instrument for the next task. This, too, unnecessarily delays the course of the operation. In addition, during the activation of a procedure errors can occur regarding the setting of appropriate operating parameters, such as a suitable HF current.

Known multifunctional instruments of the kind described above furthermore comprise poles that are electrically insulated from one another, being provided for coagulation and for cutting respectively, so that the instrument must have relatively large dimensions. This distinctly limits the surgeon's freedom of movement in the operation region and hence limits the range of functions for which the known instruments can be used.

BRIEF SUMMARY OF THE INVENTION

The present invention is directed towards the provision of an electrosurgical instrument whereby an operation, in particular one requiring several procedural components, can be performed in the simplest manner and with an optimized sequence of steps.

In particular, according to the present inventions an electrosurgical instrument is provided that comprises two branches connected in an articulated manner, which can be actuated to open or close as is appropriate for a clamping, spreading or cutting tool. The instrument further comprises electrode parts at distal ends of the branches, which are electrically insulated from one another and are used for grasping tissue and conducting a coagulation current through the tissue to coagulate it, as well as current-supply devices to deliver the coagulation current to the electrode parts. On at least one electrode part of the instrument there is additionally formed a cutting section designed as cutting electrode, so that the electrode part comprises the cutting section and a coagulation section. Furthermore, a control unit to control the HF current is provided, such that when a threshold value characterizing properties of the monitored tissue has been reached, a cutting current different from the coagulation current is supplied to at least the cutting section.

It will be appreciated that on the electrode part designed for coagulation a cutting section is disposed in such a way that at a suitable point in time, i.e. when a certain stage of the operation has been reached, it acts as cutting electrode. Therefore the surgeon is not burdened with making decisions at the transition from a coagulation phase into a subsequent cutting phase. At the same time optimal operating parameters, such as the correct current intensity, can be generated with no need for the operator to set these independently by way of the voltage at the HF generator. Thus the temporal sequence of events between the individual operation phases and the momentarily required HF current are optimally matched to one another. The operation can thus be carried out while sources of error are eliminated as far as possible.

In a first preferred embodiment switching devices associated with the control unit detect the threshold value as a specified distance between the branches, so that the cutting current is supplied in dependence on this distance. As soon as the distance between the branches, i.e. between the electrode parts, has fallen below a specified value, the cutting current is supplied at least to the cutting section. In this process the switching devices, when actuated, send to the control unit a signal that causes the latter to supply an appropriate cutting current to the cutting section, by way of a high-frequency generator. The distance serves to identify the situation in which a cutting process can be carried out, i.e. the fact that that the electrode parts are at a distance from one another such that cutting has just become possible for the first time. The distance between the electrode parts in this case can be defined by the level of the adjusted HF voltage.

The switching devices are advantageously provided on at least one of the branches and/or on a spacer disposed on at least one of the branches. This is advantageous because the distance is then detected directly by the switching devices, which can simultaneously initiate the cutting process.

In one preferred embodiment the switching devices are constructed as a push-button switch. This is then preferably attached to the spacer on the one branch, so that when the switch is touched by the opposite branch and thus when the threshold value is reached—in this case the specified distance between the electrode parts—the cutting current is supplied to the cutting section. This is a particularly simple design with which to trigger the cutting process in an economical manner, when the distance between the electrode parts becomes less than the specified value.

In another preferred embodiment the switching devices are constructed as a non-contact switch. These have the advantage that it is not necessary for the branches to touch one another, and therefore the mechanism is less vulnerable to wear and tear while operating precisely.

It is advantageous for the non-contact switches then to be designed, for example, as proximity switches or also as reed contacts. For instance, if a reed contact is attached to the one branch and a magnet to the opposite branch, then the reed contact switches as soon as the magnet is at a certain distance from the reed contact. A proximity switch operates similarly, e.g. an inductive proximity switch. The proximity switch attached to the one branch switches as soon as a metal object disposed on the opposite branch generates eddy currents in an electromagnetic alternating field of the proximity switch. In the case of a switch such as is described here, the switching distance can preferably be defined occasionally by the metal object inserted into the alternating field.

The control unit is advantageously associated with a device for resistance measurement that detects the threshold value in terms of the ohmic resistance of the tissue, so that the cutting current is supplied in dependence on this ohmic resistance. The measurement of tissue resistance enables determination of a precise point in time at or after which a cutting process can be started. As soon as the progress of the operation has caused a specific resistance to be reached within the tissue, the control unit causes the appropriate cutting current to be supplied to the cutting section. This procedure is extremely reliable because the tissue resistance, when altered by coagulation, provides a precise reference value for when a cutting process can be begun.

In another preferred embodiment the control unit is associated with an electric-arc monitor and/or current monitor that detect the threshold value in the form of an optimal time for ending coagulation, so that the cutting current is supplied in dependence on the coagulation end-point time. That is, the cutting current is supplied at least to the cutting section as soon as coagulation has been terminated on the basis of the signal provided by the corresponding monitor. Thus the supply of the cutting current advantageously occurs at a time that is ideal for the course of the operation. The ways in which the current monitor and arc monitor function are described extensively, for example, in the document EP 0 253 012 B1.

Preferably the cutting section at the at least one electrode part is constructed as a tapering region, with respect to the coagulation section of the at least one electrode part. In this case coagulation section and cutting section can constitute an integrally constructed electrode, or else the two regions are disposed independently of one another. The tapered configuration of the cutting section enables the current density from the cutting section to be increased as is required for cutting tissue. The electrode part in which the coagulation section and the cutting section are integral can act as coagulation electrode over its entire surface area, i.e. over both the surface of the coagulation section and the surface of the cutting section, whereas the tapered cutting section alone is available for a later cutting process. In the case of coagulation and cutting regions that are separate from one another, these can be employed both in combination and also separately from one another. To the smaller surface region, designed as cutting section, an adequate cutting current corresponding to the above considerations is supplied by way of the current-supply devices. Thus one and the same instrument can be used both for coagulation and also for cutting.

In one preferred embodiment the cutting section is formed on the at least one electrode part as an edge structure with a substantially triangular cross section. A triangular cross section enables the successive transition from a large surface region of the electrode part to its tapered edge section. The gradual transition is especially well suited for inserting the whole electrode part as coagulation electrode, given a tissue with adequate thickness, and at an advanced stage of the operation using the cutting section alone for cutting.

It is advantageous for the cutting section to be formed on the at least one electrode part as an edge structure with a substantially circular cross section. In this embodiment a relatively large electrode surface is available for the coagulation process, given a tissue with adequate thickness, whereas the shaped edge of the cutting section is of hardly any importance. In contrast, at an advanced stage of the operation and if the opposed electrode parts of the electrosurgical instrument are sufficiently close, because of the edge configuration of the cutting section the current density can be increased sufficiently to make possible a cutting process.

Another solution provides that the cutting section on the at least one electrode part is substantially spherical in shape. This allows the cutting surface to be kept larger and a correspondingly broad cut to be made.

The solution in accordance with the invention provides for the cutting section to have a pointed, needle or loop-type shape. This corresponds to other customary forms of cutting electrodes, so that cutting can be carried out with the instruments ordinarily used for the particular application.

In one preferred embodiment the cutting section is formed on each of the opposed electrode parts. Because here two sections are designed for cutting, an especially precise cutting action can be achieved, because the current density can be increased at both electrode parts.

The cutting section can also, however, be disposed outside the coagulation section, i.e. be constructed separately therefrom, as already mentioned above. In this case it is advantageous for the cutting section to be constructed as a component that can be moved relative to the coagulation section, by means of positioning devices. The cutting section can then be removed from the coagulation region during a coagulation process, so that no undesired cutting actions occur at this time. When the threshold value is reached, the cutting section or sections can be brought into the appropriate position, i.e. the position required for cutting.

Preferably the positioning devices comprise a two-armed lever that is rotatably mounted in one of the branches; this lever comprises a first and a second end, the first end being provided to accommodate the cutting section and the second end, to make contact with the opposite branch or a spacer situated on the opposite branch. When the second end contacts the opposite branch, the cutting section can be moved in the direction of the opposite electrode part. The positioning devices additionally comprise a readjustment means, so that the cutting section can be moved back into the starting position when contact has ended. This makes it especially simple to retract the cutting section into the coagulation section during the coagulation phase, so as to avoid impairment of the coagulation process by the cutting section. In this case, as soon as the threshold value has been reached and a contact has been made, the cutting section rotates out of its resting position. The cutting current can be supplied to the now exposed cutting section, for example by way of the switching devices, which in accordance with the above description are disposed on the spacer or at the second end of the lever and which deliver an appropriate signal to the control unit. Because of the simple mechanical construction, such a multifunctional electrosurgical instrument is economical and simple to manufacture. The positioning of the cutting section is furthermore independent of any force exerted by the surgeon's hand, because the control unit is activated exclusively on the basis of making contact. It is also possible for a positioning device such as just described to be provided on both branches.

One preferred embodiment provides for a device serving as a receptacle for the cutting section to be attached to the first end of the two-armed lever. In this case it is advantageous that the cutting section can be temporarily removed. The advantage here is obtained when the cutting section is to be cleaned after an operation phase, or when no cutting process is intended. This arrangement allows the cutting section to be inactivated in the simplest manner.

One possible implementation of the device consists in constructing the cutting section as an integral component of the first end of the two-armed lever. Thus the positioning device can be manufactured in a particularly simple way.

One preferred embodiment provides that the readjustment means for the lever arm has the form of a spring element disposed in the branch that comprises the positioning devices. A spring element is a component that is simple to install and economical, and that always fulfills the required function with hardly any wear and tear.

One solution in accordance with the invention provides that the cutting section is made of an anti-adhesion coating and/or of an erosion-resistant material. The heat developed when HF current is introduced into the tissue to be treated does not only cause the desired coagulation or cutting effects. In addition, for instance, tissue remnants and blood can become burned onto the electrode parts of the clamps, in particular, so strongly as to impair the current flow. An anti-adhesion coating reduces such contamination and should be provided in particular at each cutting section. A layer of erosion-resistant material can additionally protect the cutting section from wear and tear caused by the high HF current.

Exemplary embodiments of the invention will now be described in greater detail with reference to the accompanying drawings.

BRIEF DESCRIPTION OF THE DRAWINGS

FIG. 1 is a schematic end view of an electrode arrangement in a first embodiment of electrosurgical instrument according to the invention.

FIG. 2 is a view similar to that of FIG. 1 but of a second embodiment of instrument.

FIG. 3 is a view similar to that of FIG. 1 but of a third embodiment of instrument.

FIG. 4 is a view similar to that of FIG. 1 but of a fourth embodiment of instrument.

FIG. 8b is a voltage/time diagram in which the time course of the voltage is represented for the various operational modes represented in FIG. 8a.

DETAILED DESCRIPTION OF THE INVENTION

Figure 5:
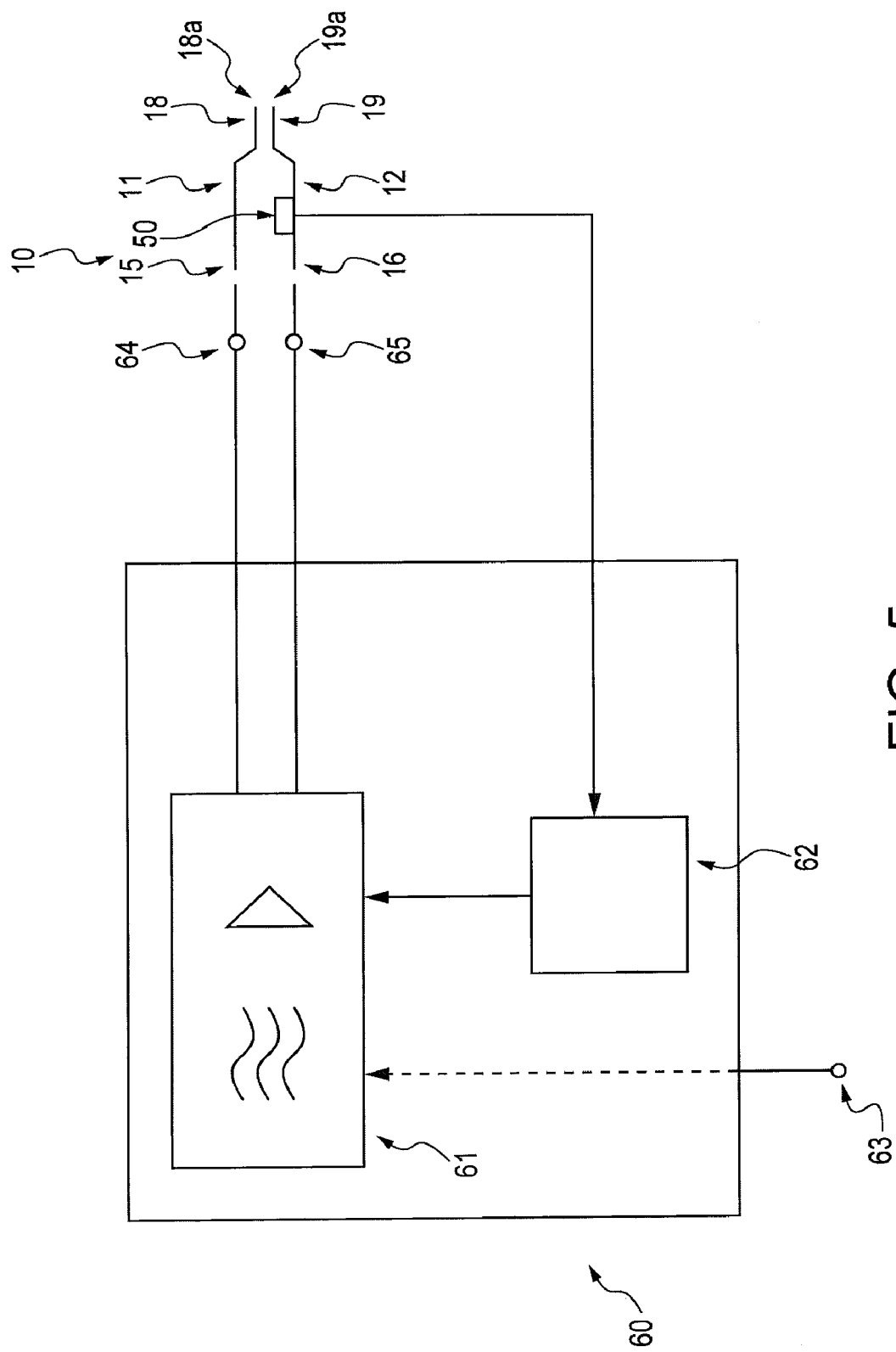
FIG. 5 is a functional block diagram of an embodiment of electrosurgical instrument according to the invention.

In the following description, the same reference numerals are used for identical parts or parts with identical actions.

FIGS. 1 to 3 show various embodiments of an arrangement of electrode parts 18, 19 situated opposite one another. In each case, an explicit cutting section 18a is formed on only one electrode part 18. It should be pointed out that these are schematic drawings, which show a front view of only the electrode parts 18, 19. The electrosurgical instrument 10 that incorporates the electrode parts 18, 19 is not shown here.

Formation of the cutting section 18a can ideally be achieved by tapering the associated electrode part 18, so that the electrode part 18 ultimately comprises a coagulation section 18b and a cutting region, i.e. the cutting section 18a. The reduction of the electrode surface allows the current density to be increased at the cutting section 18a, as is required for cutting tissue. The electrode part 18 comprising the integral coagulation section 18b and cutting section 18a can act as the coagulation electrode over the entire surface area during a coagulation process, i.e. over both the surface area of the coagulation section 18b and that of the cutting section 18a, whereas the tapered cutting section 18a alone is available for a later cutting process. For the cutting process it is provided that a cutting current different from the coagulation current is supplied to the cutting section 18a.

If the cutting section 18a is an edge structure with a triangular cross section, as shown in FIG. 1, the gradual transition from a large surface area to the tapered edge region makes it possible to a particularly great degree for the entire electrode part 18 to be employed as coagulation electrode, given sufficient tissue thickness, and in an advanced stage of the operation to use only the cutting section 18a for cutting.

If the cutting section 18a is formed on the at least one electrode part 18 as an edge structure with a circular cross section, as shown in FIG. 2, a relatively large electrode surface is available for the coagulation process, whereas the edge structure in the cutting section 18a is of hardly any importance, given sufficient tissue thickness. During the subsequent course of the operation, if the opposed electrode parts 18, 19 of the electrosurgical instrument 10 are sufficiently close to one another, because of the edge structure of the cutting section 18a the current density can be increased to such an extent as to make a cutting process possible.

In the case of a substantially spherical cutting section 18a at the at least one electrode part 18, as is shown in FIG. 3, the cutting surface can be made larger so that a correspondingly broad cut can be carried out.

The cutting section 18a, 19a can also be constructed in a pointed, needle-like or loop-like shape.

FIG. 4 shows an electrode arrangement in which the cutting section 18a, 19a is in each case formed on the opposed electrode parts 18, 19. Here, again, explicit coagulation sections 18b, 19b are provided at the two electrode parts 18, 19. This drawing should also be understood as merely schematic. Since there are two sections 18a, 19a designed for cutting, an especially precise cutting action can be achieved, because the current density at the two electrode parts 18, 19 can be increased.

FIG. 5 shows a functional block diagram in which the electrosurgical instrument 10 is connected to a high-frequency surgical appliance 60. The components of the HF-surgery appliance 60 illustrated here are exclusively, and hence schematically, those required to explain the invention.

The HF-surgery appliance 60 comprises an input connector 63 by way of which, for instance, actuating devices such as finger and/or foot switches (not shown) can be connected in order to activate and/or inactivate the HF current. The actuating devices here can preferably be implemented by a computer arrangement, and in practical application are connected by way of a control unit (not shown) to a HF generator 61. For the sake of simplicity the input connector 63 in this drawing is connected directly to the HF generator 61, as shown by a dashed line. On the output side of the HF-surgery appliance 60 there are provided a first output connector 64 and a second output connector 65, by way of which the electrosurgical instrument 10 can be connected.

The central component of the HF-surgery appliance 60 is the controllable HF generator 61 for producing a HF current, or stated more precisely to produce a voltage $U_{HF}$. By adjusting the voltage $U_{HF}$, the current intensities $I_{HF}$ needed for the various operational modes, such as coagulation or cutting, can be set as desired. The HF generator 61 is connected to a control unit 62. The control unit 62 is designed to receive signals from switching devices 50 disposed on the electrosurgical instrument 10.

The switching devices 50 are disposed between branches 11, 12 of the electrosurgical instrument and detect a threshold value, e.g. as a specific distance between the branches 11, 12, i.e. between the electrode parts 18, 19. The distance between the electrode parts 18, 19 serves here to characterize the fact that a cutting procedure can be carried out, and is therefore matched to the level to which the HF voltage has been set. As soon as the branches 11, 12 have been brought together to the specified distance, the switching devices 50 are actuated and conduct a signal to the control unit 62. This then initiates delivery of the appropriate cutting current from the HF generator 61 to the cutting sections 18a, 19a, by of the associated proximal ends 15, 16 of the electrosurgical instrument. It should be pointed out that here, again, the cutting section may be formed at only one or at both electrode parts 18, 19. For the following explanations it is assumed that each of the electrode parts 18, 19 comprises a cutting section 18a, 19a.

As a means of detecting the distance and activating the control unit 62 that controls the cutting current it is possible to use push-button switches but also non-contact switches, such as reed-contact or proximity switches. With contact-type switches the electrosurgical instrument can have an especially economical construction, whereas non-contact switches operate extremely precisely and are substantially free of abrasion.

Figure 7:
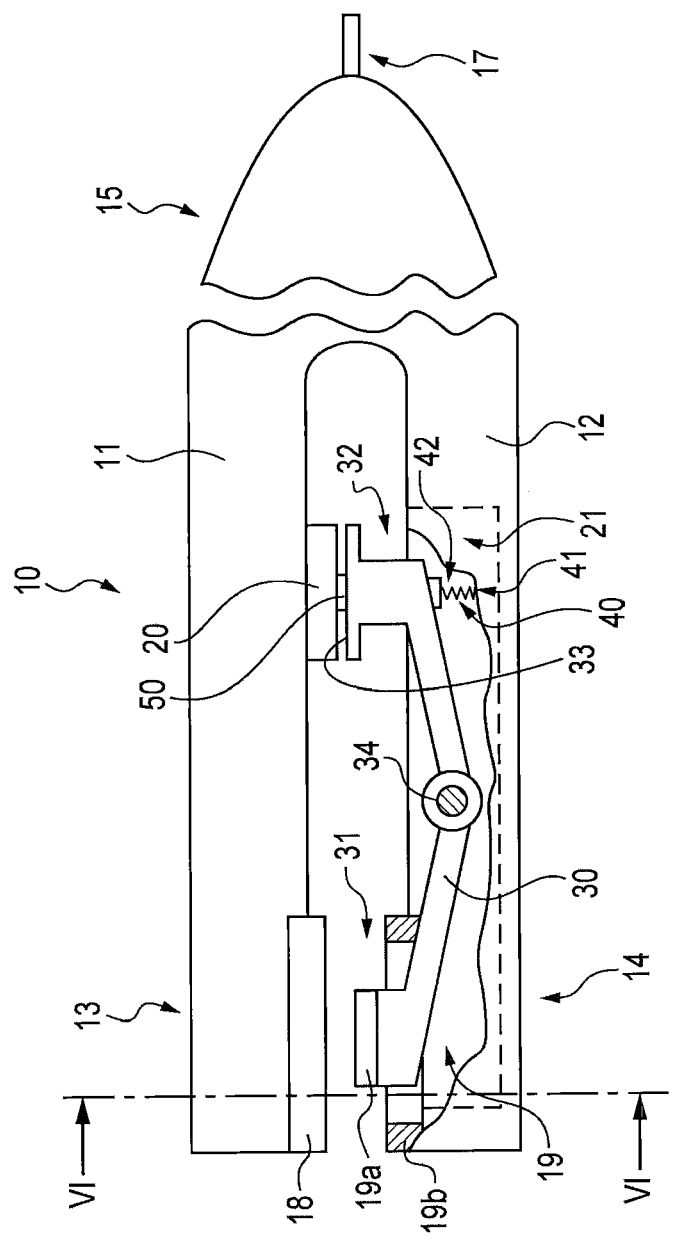
FIG. 7 is a side view of the electrode arrangement shown in to FIG. 6.
Figure 6:
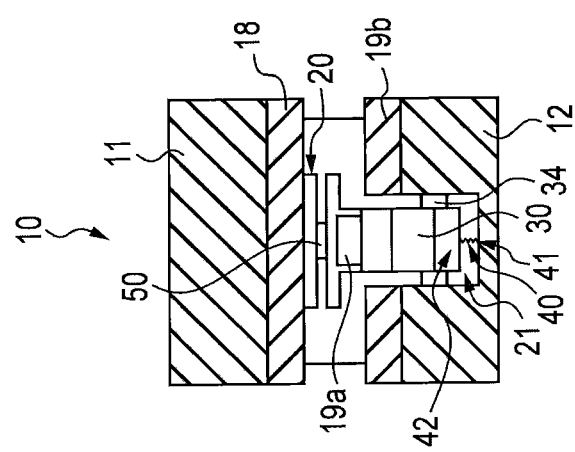
FIG. 6 is a sectional view, along the line VI-VI in FIG. 7, of an electrode arrangement in a fifth embodiment of instrument.

Regarding the exact arrangement of the switching devices, reference is made to the description of FIGS. 6 and 7.

The threshold value can also be detected, for example, by way of a device for resistance measurement (not shown) associated with the control unit 62. As soon as the operation has proceeded to the point at which a specific resistance in the tissue has been reached, the control unit 62 causes an appropriate cutting current to be supplied to the relevant cutting section 18a, 19a. Accordingly, the threshold value is specified in terms of an ohmic resistance.

It is also possible for the control unit 62 to be equipped with an electric-arc monitor and/or a current monitor (not shown), so that the threshold value can be detected as the optimal time to terminate coagulation. The cutting current is then supplied to at least the relevant cutting section 18a, 19a as soon as coagulation has been stopped because of the signal provided by the corresponding monitor. Hence delivery of the cutting current advantageously occurs at a time that is optimal for the experimental procedure. The ways in which the current monitor and arc monitor function are described in detail, for example, in the document EP 0 253 012 B1.

FIG. 6 shows an electrode arrangement in a fifth embodiment, as sectional view along the line VI-VI in FIG. 7. FIG. 7 shows a side view of the electrosurgical instrument 10 according to FIG. 6. The electrosurgical instrument 10 is designed here as a tweezers-shaped instrument.

In these figures distal ends 13, 14 of the branches 11, 12 of the electrosurgical instrument 10 are illustrated, as well as the associated electrode parts 18, 19. As can be seen in particular in FIG. 7, within one branch 12 a two-armed lever 30 with a first end 31 and a second end 32 is seated so as to be rotatable about an axle 34; the first end 31 is provided as a holder for the cutting section 19a, and the second end 32 is provided to make contact with the opposite branch 11 or a spacer 20 disposed on the opposite branch 11. Here the lever 30 assists positioning of the cutting section 19a, so that the latter can be moved relative to the section 19b provided for the purpose of coagulation. That is, in this embodiment the electrode part 19 consists of two independent sections, the coagulation section 19b and the cutting section 19a.

So that the lever 30 can be seated in the branch 12, the latter comprises a recess 21 into which the first end 31 of the lever 30 can be embedded, preferably so as to be completely enclosed. The recess is formed both in the coagulation section 19b of the branch 12 and in the branch 12 itself. Because this arrangement enables the cutting section 19a to be embedded in a recess, the possibility that the cutting section 19a will interfere with the coagulation electrode 19b during the coagulation process is avoided.

As the branches 11, 12 are being moved towards one another by the operator, the spacer 20 continuously approaches the second end 32 of the lever 30. The second end 32 in this embodiment comprises a bearing surface 33. As soon as the spacer 20 on the opposite branch 11 comes into contact with the bearing surface 33, the first end 31 of the lever 30 is lifted out of a resting position, emerging from the branch 12, so that the cutting section 19a projects out of the coagulation electrode 19b. The cutting section 19a and the opposite electrode part 18 can now cooperate with one another in a cutting phase. For this purpose the spacer 20 or the bearing surface 33 comprise the switching devices 50 described in detail above. When the spacer 20 or the bearing surface 33 makes contact with the switching devices 50, actuation of the latter causes the corresponding cutting current to be supplied to the cutting section 19a by way of current-supply devices 17, as likewise described above.

In the branch 12 containing the lever 30 a spring element 40 is provided. This is connected at a first end 41 to the branch 12 and at a second end 42 to the second lever end 32. Because the bearing surface 33 of the second lever end 32 is in contact with the spacer 20 of the opposite branch 11, and/or with the switching devices 50 disposed on the spacer 20 or the bearing surface 33, the spring 40 attached to the second lever end 32, e.g. a spiral spring, is compressed. As soon as the contact is broken, the spring 40 moves the lever 30 back into its resting position, so that the lever end 31 bearing the cutting section 19a sinks back into the branch 12. The coagulation electrode 19b is thus again made available to coagulate tissue. The spring element 40 is an economical component that is simple to install and always performs the required function with hardly any wear and tear.

The switching devices 50 can furthermore also be positioned at other places on the branches 11, 12. In this case non-contact switches would be especially worth consideration, as they communicate a signal to the control unit when a specified distance between the electrode parts 18, 19 has been reached, even without any direct contact.

The first end of the two-armed lever 31 can comprise a receptacle for the cutting section 19a, so that the latter can be readily removed from the electrosurgical instrument, e.g. for the purpose of cleaning. Alternatively, it is possible to make the first lever end 31 integral with the cutting section 19a, which results in a device that is extremely economical to manufacture.

Because of the simple mechanics of the positioning device 30 just described for the cutting section 19a, a multifunctional electrosurgical instrument 10 can be manufactured in a simple and economical manner.

The cutting section 18a, 19a can preferably be constructed with an anti-adhesive coating and/or with a layer of abrasion-resistant material. This avoids the possibility that tissue will be burnt onto the cutting section, or that the material will wear out.

Figure 8A:
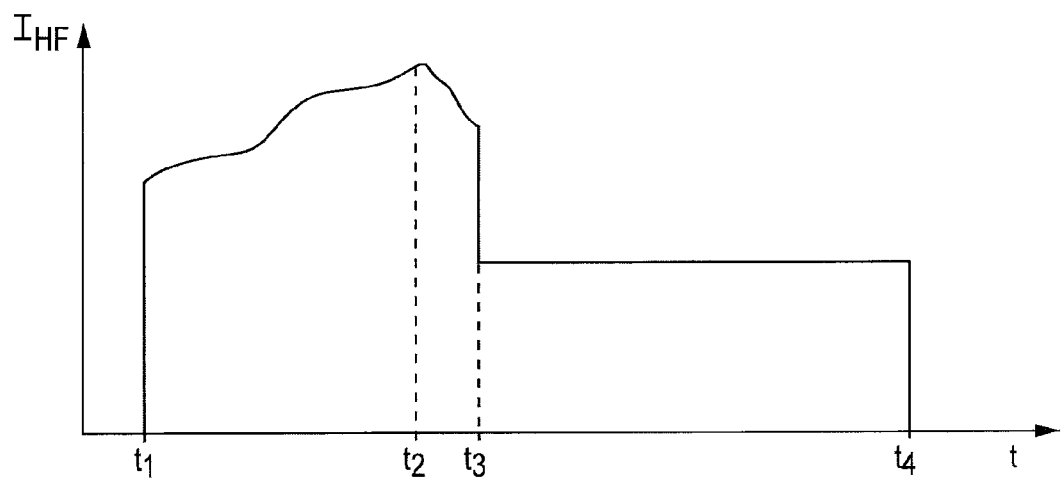
FIG. 8a is a current/time diagram in which the time course of the current intensity is represented for different operational modes of an electrosurgical instrument according to the invention.
Figure 8B:
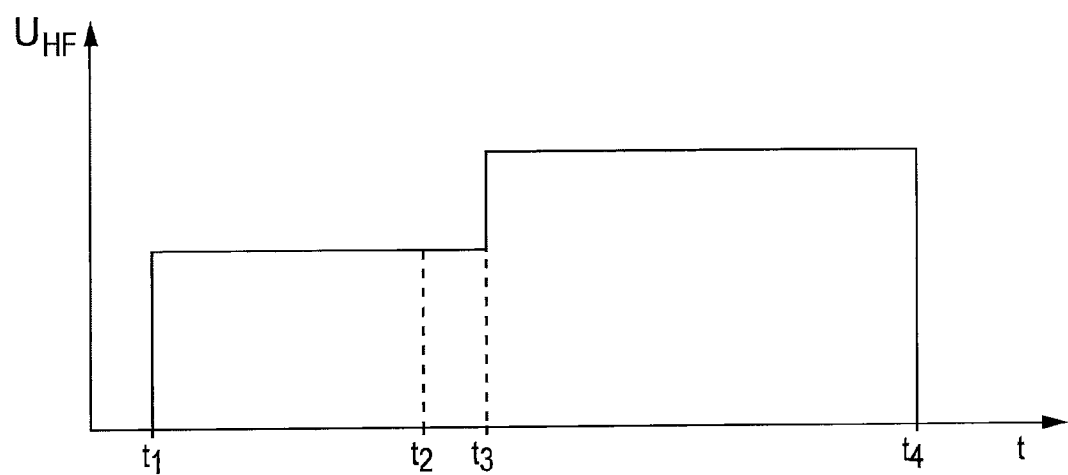

FIG. 8a is a diagram illustrating the typical variation in intensity of the HF current in dependence on different modes of operation. On the ordinate is shown the current intensity $I_{HF}$ and on the abscissa, the time t. FIG. 8b is the voltage/time diagram corresponding to FIG. 8a. Here the ordinate shows the voltage $U_{HF}$ and the abscissa, again, the time t. Because both figures are schematic illustrations, the units are not shown.

According to FIG. 8a, at a time $t_1$ a coagulation mode is switched on and the current begins to flow through the tissue to be coagulated. As the tissue becomes warmer, the current intensity $I_{HF}$ increases, until a time $t_2$. From the time $t_2$ on, the tissue begins to coagulate, and hence a vaporization phase is initiated. Because of the heat development associated with the HF current, a specified region of tissue can be altered or destroyed by protein coagulation and dehydration. In this process, the colloidal components of the tissue that had been present in solution first enter the gel state, and then as gel components they lose fluid and so become still more compact; the tissue is "cooked". The resistance of the tissue rises accordingly, so that because of the falling conductivity of the tissue the current intensity $I_{HF}$ decreases until a time $t_3$. When the drying of the tissue has reached a certain stage, coagulation comes to a halt. Between the times $t_3$ and $t_4$, a cutting mode is activated. During this period, the graph shows a relatively constant level of current intensity $I_{HF}$, because the tissue resistance remains substantially the same throughout the cutting process.

As shown in FIG. 8b, the HF generator is set to a particular voltage $U_{HF}$ for the time interval $t_1$ to $t_3$. The cutting mode that follows the coagulation mode requires an increase in this voltage $U_{HF}$ between the times $t_3$ and $t_4$. The current intensity $I_{HF}$ is ultimately dependent on the level to which the voltage $U_{HF}$ has been set and on the resistance of the already coagulated tissue. At the time $t_4$ the cutting mode can be terminated, for example by an automatic switching-off device.

LIST OF REFERENCE NUMERALS

10 Electrosurgical instrument
11 Clamp part, branch
12 Clamp part, branch
13 Distal end
14 Distal end
15 Proximal end
16 Proximal end
17 Current-supply devices
18 Electrode part
18a Cutting section, cutting electrode
18b Coagulation section, coagulation electrode
19 Electrode part
19a Cutting section, cutting electrode
19b Coagulation section, coagulation electrode
20 Spacer
21 Recess
30 Two-armed lever, positioning device
31 First end of lever
32 Second end of lever
33 Bearing surface
34 Axis of rotation
40 Spring element
41 First end of spring element
42 Second end of spring element
50 Switching devices
60 HF-surgery appliance
61 HF generator
62 Control unit
63 Input connector
64 First output connector
65 Second output connector

The invention claimed is:

1. An electrosurgical instrument comprising
    two branches which are joined to one another in an articulated manner and which are adapted to open and to close in a scissor-like manner;
    electrode parts located at distal ends of the branches and which are electrically insulated from one another and which are adapted to grasp tissue and to pass a coagulation current through the tissue for the purpose of coagulating the tissue;
    current-supply devices adapted to supply said coagulation current to said the electrode parts;
    a cutting section located on at least one said electrode part and adapted to operate as a cutting electrode whereby said one electrode part comprises said cutting section and a coagulation section; and
    a control unit adapted to control high frequency current in such a way that when a threshold value characterizing a particular property of grasped tissue has been reached, a cutting current different from said coagulation current is supplied to at least said cutting section,
    wherein the two branches are oppositeely situated,
    wherein the cutting section is constructed as a component that can be moved relative to the coagulation section by means of positioning devices, the positioning devices comprising a two-armed lever rotatably seated in one of the two branches, the two-armed lever having a first end and a second end, such that the first end is provided to accommodate the cutting section and the second end is provided to make contact with at least one of the oppositely situated other of said branches and a spacer disposed on the oppositely situated other of said branches, such that when contact is made, the cutting section can be moved in the direction of the opposite electrode part, and a readjustment device adapted to move said cutting section back into its initial position after said contact period has ended.

2. Electrosurgical instrument according to claim 1, comprising switching devices associated with said control unit and adapted to detect said threshold value as a predetermined distance between said branches in order that said cutting current is supplied dependent on the distance between said branches.

3. Electrosurgical instrument according to claim 2, wherein said switching devices are provided on at least one of the branches and the spacer.

4. Electrosurgical instrument according claim 2, wherein said switching devices are constructed as a push-button switch.

5. Electrosurgical instrument according to claim 2, wherein said switching devices are constructed as non-contact switches.

6. Electrosurgical instrument according to claim 5, wherein said non-contact switches are constructed as at least one of a proximity switch and a reed contact.

7. Electrosurgical instrument according to claim 1, wherein said control unit comprises a device for resistance measurement, which detects said threshold value as an ohmic resistance of the tissue whereby said cutting current is supplied dependent on the ohmic resistance.

8. Electrosurgical instrument according to claim 1, wherein said control unit comprises at least one of an electric-arc monitor and a current monitor, which detect said threshold value as an optimal time to terminate coagulation whereby said cutting current is supplied dependent on a coagulation termination time.

9. Electrosurgical instrument according to claim 1, wherein said cutting section located on the at least one electrode part tapers with respect to said coagulation section of the at least one electrode part.

10. Electrosurgical instrument according claim 1, wherein said cutting section comprises an edge structure defining a substantially triangular cross section on the at least one electrode part.

11. Electrosurgical instrument according to claim 1, wherein said cutting section comprises an edge structure with a substantially circular cross section on the at least one electrode part.

12. Electrosurgical instrument according to claim 1, wherein said cutting section comprises a substantially spherical shape on the at least one electrode part.

13. Electrosurgical instrument according to claim 1, wherein said the shape of said cutting section is selected from the group comprising of pointed, needle-like and loop-like.

14. Electrosurgical instrument according to claim 1, wherein said cutting section is constructed on each of the two oppositely situated electrode parts.

15. Electrosurgical instrument according to claim 1, wherein said first end of the two-armed lever defines a receptacle in which said cutting section is attached.

16. Electrosurgical instrument according to claim 1, wherein said cutting section is an integral component of said first end of the two-armed lever.

17. Electrosurgical instrument according to claim 1, wherein said readjustment device comprises a spring element disposed in the branch that comprises the positioning devices.

18. Electrosurgical instrument according to claim 1, wherein said cutting section comprises at least one of an anti-adhesion coating and erosion-resistant material.

* * * * *